(12) United States Patent
Nanjan et al.

(10) Patent No.: US 8,748,467 B2
(45) Date of Patent: Jun. 10, 2014

(54) TOPICAL FORMULATION

(75) Inventors: Karthigeyan Nanjan, Auckland (NZ); Fadil Al Alawi, Auckland (NZ); Paul Chambers, Palmerston North (NZ); Kate Hill, Palmerston North (NZ)

(73) Assignee: Bayer Intellectual Property GmbH, Monheim (DE)

(*) Notice: Subject to any disclaimer, the term of this patent is extended or adjusted under 35 U.S.C. 154(b) by 614 days.

(21) Appl. No.: 12/524,421

(22) PCT Filed: Jan. 22, 2008

(86) PCT No.: PCT/NZ2008/000011
§ 371 (c)(1),
(2), (4) Date: Dec. 16, 2009

(87) PCT Pub. No.: WO2008/091167
PCT Pub. Date: Jul. 31, 2008

(65) Prior Publication Data
US 2010/0137389 A1    Jun. 3, 2010

(30) Foreign Application Priority Data
Jan. 24, 2007   (NZ) ................................... 552816

(51) Int. Cl.
*A01N 43/50*    (2006.01)
*A61K 31/415*   (2006.01)

(52) U.S. Cl.
USPC .......................................... 514/392; 514/784

(58) Field of Classification Search
None
See application file for complete search history.

(56) References Cited

U.S. PATENT DOCUMENTS

| | | | |
|---|---|---|---|
| 5,091,182 A | 2/1992 | Ong et al. | |
| 5,296,222 A | 3/1994 | Petersen et al. | |
| 5,556,754 A | 9/1996 | Singer et al. | |
| 5,871,950 A | 2/1999 | Singer et al. | |
| 5,919,436 A | 7/1999 | Fuller | |
| 2002/0058068 A1 | 5/2002 | Houze et al. | |
| 2003/0170195 A1 | 9/2003 | Houze et al. | |
| 2005/0209295 A1 | 9/2005 | Kohn et al. | |
| 2006/0160733 A1 | 7/2006 | Chaudhry et al. | |
| 2006/0233870 A1 | 10/2006 | Houze et al. | |
| 2006/0240087 A1 | 10/2006 | Houze et al. | |

FOREIGN PATENT DOCUMENTS

| | | |
|---|---|---|
| CN | 1085079 | 4/1994 |
| WO | 97/43989 | 11/1997 |
| WO | WO 2005009510 A2 * | 2/2005 |
| WO | WO 2006/122472 A1 | 11/2006 |
| WO | WO 2007/016766 A1 | 2/2007 |

OTHER PUBLICATIONS

Magnusson et al "Veterinary drug delivery: potential for skin permeation enhancement", Advanced Drug Delivery Reviews, 50 (2001), 205-227.*
Tenjarla et al "Evaluating the irritation potential of skin permeation enhancers in the hairless guinea Pig", 1995, vol. 14, Vo. 4, pp. 299-307.*
Derwent Abstract Accession No. 95-200804/27, and CN 1085079A (Chen, L. Xu, D) Jul. 24, 1993. Abstract.
Hoffmann, S.B. et al. "Bioavailability of transdermal methimazole in a pluronic lecithin organogel (PLO) in health cats." J.Vet.Pharmacol. Therap. (2002) 25:189-193. Introduction, Methimazole Formulations and Discussion.
Hoffman, G. et al. "Transdermal methimazole treatment in cats with hyperthyroidism." J. Feline Medicine and Surgery. (2003) 5:77-82.
Sartor, L.L. et al. "Efficacy and Safety of Transdermal Methimazole in the Treatment of Cats with Hyperthyroidism" J.Vet.Intern.Med. (2004) 18:651-655.
Lecuyer, M. et al. "Clinical Efficacy and Safety of Transdermal Methimazole in the Treatment of Feline Hyperthyroidism." Can.Vet. J. (2006) 47:131-135.
Buijetels, J.J.C.W.M. et al. "Transdermal Carbimazole for the Treatment of Feline Hyperthyroidism" Tijdschr.Diergeneeskd. (2006) 131:478-482.
International Search Report prepared by the Australian Patent Office on May 15, 2008 for International Application No. PCT/NZ2008/000011.
Written Opinion prepared by the Australian Patent Office on May 15, 2008 for International Application No. PCT/NZ2008/000011.
International Preliminary Report on Patentability prepared by the Australian Patent Office on Oct. 24, 2008, for International Application No. PCT/NZ2008/000011.
Kasraee Behrooz et. al, "Topical Methimazole as a new Treatment for Post Inflammatory Hyperpigmentation: Report of the First case." Dermatology, S. KargerAG, CH, vol. 211, No. 4,Jan. 1, 2005, pp. 360-362, XP009129682 ISSN: 1018-8665.
"16th ECVIM-CACongress" Amsterdam, Netherlands, Journal of Veterinary Internal Medicine, Lippincott, Philadelphia, US, vol. 20, No. 6, Sep. 14, 2006, pp. 1515-1539, XP009129678 ISSN: 0891-6640.
Elias A N et. al, "A Controlled Trial of Topical Propylthiouracil in the Treatment of Patients with Psoriasis." Journal of the American Academy of Dermatology, vol. 31, No. 3, Part 1, 1994, pp. 455-458, ISSN: 0190-9622.

\* cited by examiner

*Primary Examiner* — Wu-Cheng Winston Shen
*Assistant Examiner* — Jean Cornet

(57) ABSTRACT

The invention relates to composition and related therapeutic methods including at least one antihyperthyroid drug formulated for transdermal administration. Because the formulation is formulated for transdermal administration, the formulation is easier to administer than existing formulations which are administered orally to animals. Issues surrounding transdermal administration versus oral administration have also been resolved allowing the agent to remain stable during storage and retain a high level of efficacy.

8 Claims, 1 Drawing Sheet

TOPICAL FORMULATION

CROSS REFERENCE TO RELATED APPLICATIONS

This application is a national stage application under 35 U.S.C. 371 of PCT Application No. PCT/NZ2008/000011 having an international filing date of 22 Jan. 2008, which designated the United States, which PCT application claims the benefit of New Zealand Application No. 552816 filed 24 Jan. 2007, the entire disclosure of each of which are hereby incorporated herein by reference.

STATEMENT OF CORRESPONDING APPLICATIONS

This application is based on the Provisional specification filed in relation to New Zealand Patent Application Number 552816, the entire contents of which are incorporated herein by reference.

TECHNICAL FIELD

The invention relates to a topical formulation. More specifically the invention relates to a topically applied formulation for the administration of an antihyperthyroid drug compound.

BACKGROUND ART

Clinical hyperthyroidism as a result of benign hyperplasia of the thyroid is a very common condition in old cats (Feldman and Nelson, 1996) and is stated as being the most common endocrine disorder in cats (Buijtels et al., 2006).

The average age of cats with hyperthyroidism is twelve to thirteen years. The most common phenomenon with hyperthyroidism is an increase of weight loss, in spite of greater appetite.

Cats with hyperthyroidism can be treated in three different ways. These are:
 1) Destruction of the hyper functioning gland tissue by the administration of radioactive iodine;
 2) Surgical removal of the abnormal gland tissue (thyroidectomy);
 3) Treatment with medication inhibitors of the synthesis of gland hormone (antihyperthyroid drugs).

Surgery has traditionally been the main treatment, but has a significant incidence of unwanted effects, and does not deal with the 9% of cats with ectopic thyroid tissue (Naan et al., 2006). Radioactive iodine is probably the treatment of choice as it has been shown to prolong survival time (Milner et al., 2006), but has all the drawbacks involved in handling radioactive substances safely.

This makes pharmaceutical treatment an attractive option (Trepanier, 2006) however, antihyperthyroid drugs must be administered for life, one to three times per day. This may be difficult as cats in particular are notoriously hard to dose with oral drugs such as tablets or even liquids.

Because of this, many compounding pharmacies around the world have started formulating drugs into gels which are applied to the inner side of the ear of the cat which aim to be absorbed through the skin for systemic action.

Not all drugs are suitable for transdermal penetration and only a few have been studied to determine whether they reach therapeutic levels after absorption by this route. The drug needs to be highly lipophilic and formulated in the correct vehicle for transdermal absorption (Riviere et al., 2001).

Methimazole has been used to treat hyperthyroidism in cats in the USA in tablet form. Due to difficulties with pharmacokinetics, the tablet needs to be administered repeatedly.

Carbimazole is a more lipid soluble prodrug of methimazole and is used in tablets to treat hyperthyroidism in cats in New Zealand. Neither carbimazole or methimazole are registered for use in animals in New Zealand, but veterinarians are able to prescribe them for treatment of hyperthyroidism under veterinary discretionary use of human medicines.

Methimazole has been used in a transdermal preparation of pluronic lecithin organogel (PLO). However transdermal absorption was poor in pharmacokinetic studies but it did show clinical efficacy in some cats with repeated applications (Lecuyer et al., 2006; Sartor et al., 2004; Hoffmann et al., 2003, 2002). This clinical efficacy may be due to repeated application of the gel on the same site, which could have resulted in irritation of the skin and enhanced drug absorption through the breached skin barrier. Substantial skin irritation after application of PLO for several days has been reported. Another possible explanation of the clinical effects is that they are due to oral ingestion of the PLO during grooming (Murdan, 2005).

It was also reported (Lecuyer et al, 2006) that a third of the owners of cats in their study noted a non-homogenous texture develop in the PLO gel caused by drug precipitation. It was thought this could cause a variation in drug concentration between doses.

A transdermal carbimazole formulation has recently been shown to reduce tT4 concentrations in cats (Buijtels et al., 2006). The formulation used for delivery of carbimazole is described as being eye ointment solution and lecithin. It is the inventors finding that eye ointments are made to not be absorbed directly, rather they are used to transfer the active agent from the ointment into the tear ducts. In the present invention, the inventors have found that it is desirable to not only deliver the active agent transdermally, but also to deliver the whole formulation transdermally to ensure complete absorption and full efficacy. The inventors have also found that use of lecithin is undesirable, as lecithin tends to give the formulation a thick gel texture which is sticky to handle and also does not have good absorption characteristics.

Further, as noted in Buijtels et al, it is difficult to select a penetration enhancer for a given permient. Penetration enhancer potencies tend to be drug specific or at least only predictable for a series of permients with similar physiochemical properties. Therefore, the findings in Buijtels et al should not be seen as indicative that all transdermal formulations will provide similar efficacy.

In view of the above several patents are now discussed.

U.S. Pat. Nos. 5,871,950 and 5,556,754 describe the use of methimazole to suppress expression of MHC Class 1 molecules in the treatment of autoimmune diseases. Column 18, lines 28-32 (U.S. Pat. No. 5,871,950) and column 18, lines 50-54 (U.S. Pat. No. 5,556,754) state that "The MHC class 1 suppressing drugs (of which methimazole is included as one example) may be administered as a sterile pharmaceutical composition further comprising a biological carrier including, but not limited to saline, buffer, dextrose, ethanol and water". Ethanol is described but there is no suggestion or teaching that the ethanol acts as a penetration enhancer. Ethanol and the other biological carriers listed are commonly used in injectable compositions and that is the implied use in these patents. Further, U.S. Pat. Nos. 5,871,950 and 5,556,754 state that the MHC class 1 suppressing drugs may be administered by "topical application", however there is no further teaching of a means by which this could be accomplished. As noted above, penetration enhancer potencies tend to be drug specific or at least only predictable for a series of permients with similar physio-chemical properties and therefore the teachings of U.S. Pat. Nos. 5,871,950 and 5,556,754 are vague if at all on specifics formulations to achieve the objective of a formulation for transdermal delivery of an antihyperthyroidism drug.

US 2005/0209295 describes the use of methimazole and derivatives for inhibition and prevention of cell adhesion and cell adhesion mediated pathologies. The specification teaches that the compounds may be formulated into pharmaceutical compositions that may be administered topically (among other routes). The specification goes on to state that "topically-transdermal patches may be used", and in paragraph 36 goes on to list possible pharmaceutical carriers. However there are no examples of transdermal formulations or any data that the drugs can actually be carried over the dermal barrier.

US 2006/0240087, US 2003/0170195, US 2006/0233870 and US 2002/0058068 describe transdermal administration of a drug by administration of a composition comprising a blend of two or more acrylic-based polymers having differing functionalities so as to modulate the drug solubility and hence the delivery rate. The specifications, list methimazole as a preferred drug for use in the invention, however the previous paragraphs also contains lists of drugs the authors reference the Merck index as "suitable for dermal administration". The specifications go on to give an extensive list of "penetration enhancers" for use in the inventions. However, only a limited number of those compounds listed are shown to be effective in the examples and there are no examples using methimazole or any other antihyperthyroid drug. As noted above, penetration enhancer potencies tend to be drug specific or at least only predictable for a series of permients with similar physio-chemical properties and hence without examples the compounds taught in US 2006/0240087, US 2003/0170195, US 2006/0233870 and US 2002/0058068 can only be seen as mere speculation.

To summarize, since alternative treatment for hyperthyroidism is either potentially dangerous to the cat (surgery) or to its handlers (radioactive iodine), a formulation of an antihyperthyroid drug which can be administered in a stress-free way would be a major benefit to small animal practice.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

The invention broadly relates to transdermal formulations for delivery of antihyperthyroid drugs.

According to one aspect of the present invention there is provided a composition formulated for transdermal administration including at least one antihyperthyroid drug and;
    characterized in that the composition also includes at least one penetration enhancer selected from: fatty acids, terpenes, pyrrolidones, a $C_2$-$C_8$ alcohol, glycol ethers, acetins, triglycerides and combinations thereof.

According to a further aspect of the present invention there is provided a method of treatment of hyperthyroidism in an animal in need thereof by transdermal administration of a composition including at least one antihyperthyroid drug and;
    characterized in that the composition also includes at least one penetration enhancer selected from: fatty acids, terpenes, pyrrolidones, a $C_2$-$C_8$ alcohol, glycol ethers, acetins, triglycerides and combinations thereof.

According to a further aspect of the present invention there is provided the use of a composition formulated for transdermal administration including at least one antihyperthyroid drug in the manufacture of a medicament for treatment of hyperthyroidism in an animal in need thereof and;
    characterized in that the composition also includes at least one penetration enhancer selected from: fatty acids, terpenes, pyrrolidones, a $C_2$-$C_8$ alcohol, glycol ethers, acetins, triglycerides and combinations thereof.

For the purposes of this specification, the term 'antihyperthyroid drug' is defined as any drug that inhibits production of thyroid hormone. Preferably, the antihyperthyroid drug is a thioamide. More preferably the thioamide is an imidazole. Most preferably the antihyperthyroid drug is carbimazole, methimazole, and combinations thereof. Alternatively the thioamide is a uracil such as propylthiouracil, methylthiouracil, benzylthiouracil and combinations thereof. In preferred embodiments, the composition contains approximately 5-10 mg per dose of antihyperthyroid drug, although this should not be seen as limiting as the amount of drug used may vary depending on the animal, the drug used, the degree of hyperthyroidism exhibited and so on.

For the purposes of this specification, the term 'penetration enhancer' refers to the compound or compounds improving penetration through the skin or at least the stratum corneum. In preferred embodiments, the transdermal enhancer speeds delivery of the agent through the skin such that no trace of the composition is apparent on the exterior of the skin within approximately 10 minutes after administration.

Preferably where a fatty acid is used as a penetration enhancer the fatty acid is selected from oleic acid, linoleic acid, palmitic acid and combinations thereof.

Preferably where a terpene is used as a penetration enhancer the terpene is d-limonene.

Preferably, where a pyrrolidone compound is used as a penetration enhancer, the pyrrolidone compound is selected from: n-methyl-pyrrolidone (also known as NMP or Pharmasolve), 2-pyrrolidone, and combinations thereof.

Preferably, where a $C_2$-$C_8$ alcohol is used as a penetration enhancer, the $C_2$-$C_8$ alcohol is selected from: ethanol, propanol, isopropanol, butanol, benzyl alcohol, and combinations thereof.

Preferably, where a glycol ether is used as a penetration enhancer, the glycol ether is selected from: diethylene glycol monomethyl ether, diethylene glycol monobutyl ether, dipropylene glycol monomethyl ether, and combinations thereof.

Preferably where an acetin is used as a penetration enhancer the acetin is triacetin, diacetin and combinations thereof.

Preferably where a triglyceride is used as a penetration enhancer the triglyceride is a medium chain triglyceride.

In one embodiment, the penetration enhancer also acts as a carrier and emulsifier.

One advantage found by the inventors is that the formulation of the present invention maintains drug plasma levels over a longer time frame than oral tablet treatments. This finding was unexpected since the treatment of the invention was only applied once daily whereas it is standard practice to give the oral carbimazole twice daily. The longer duration gives considerable advantages for animal welfare given that the animal need not be administered a tablet twice daily which will often result in stress for the animal. Reducing the stress to the animal and owner as well as improving the convenience of the treatment will result in a more effective treatment method since the owner will be more likely to carry out and be consistent with the treatment plan.

A further advantage of the present invention is that it is possible to make a formulation according to the invention which is stable when stored over time. For the purposes of this specification, the term 'stable' refers to at least 3 months (preferably over 9 months) chemical stability (e.g. within ±10% w/w active compound of the stated composition) of active compound when stored at 25° C. or below and at ambient humidity and of a reasonable physical stability such that the composition is substantially homogeneous and minimal separation, crystallization or turbidity in the formulation is observed.

In an alternative embodiment, the composition substantially as described above also includes at least one carrier compound. Preferably, the carrier compound includes at least one lipid soluble carrier.

For the purposes of this specification, the term 'transdermal carrier' includes compounds that solubilize the drug. Preferably, the carrier is also miscible in water including being miscible in extra-cellular and/or cellular fluids. In preferred embodiments, carrier compounds include: propylene glycol, polyethylene glycol (PEG) including PEG 4000, dimethyl formamide (DMF), cyclodextrin compounds, and combinations thereof. Note that propylene glycol may act as both a penetration enhancer and carrier.

Based on the inventor's experience, the composition may be a viscous gel or ointment. A higher viscosity gel or ointment is preferred as in the inventors experience, this prevents the animal from shaking off the gel or ointment once administered. In addition, a viscous gel or ointment also ensures that the gel or ointment remains on the administration area and does not drip or fall off onto other areas.

In one embodiment, it is envisaged that the composition would be packaged within a tube and administered by dispensing a portion of the composition from the tube and rubbing this onto the skin of the animal being treated.

In the case of a cat, it is preferable that the composition be administered to the inside skin of the ear. Administration inside the ear for a cat is preferred as it is a difficult place for the cat to reach and remove the composition as the cat cannot easily lick the inside ear. Other areas for administration include via other exposed skin areas of the animal body.

Preferably, the animal to which the composition is administered is a cat. It should be appreciated that other animals (including humans) may also be treated using the composition as described.

According to a further aspect of the present invention there is provided a veterinary composition formulated for transdermal administration including:
(a) at least one antihyperthyroid drug selected from: methimazole, carbimazole, and combinations thereof;
(b) at least one compound selected from: fatty acids, terpenes, pyrrolidones, a $C_2$-$C_8$ alcohol, glycol ethers, acetins, triglycerides and combinations thereof;
(c) propylene glycol; and
(d) PEG 4000.

According to a further aspect of the present invention there is provided a veterinary composition formulated for transdermal administration including:
(a) methimazole;
(b) oleic acid;
(c) N-methyl-pyrrolidone;
(d) propylene glycol; and
(e) PEG 4000.

According to a further aspect of the present invention there is provided a method of manufacturing a composition formulated for transdermal administration by the steps of:
(a) heating propylene glycol to a temperature of 50-60° C.;
(b) dissolving PEG 4000 into the propylene glycol;
(c) mixing in at least one compound selected from: d-limonene, N-methyl-pyrrolidone, ethanol, triacetin, and combinations thereof;
(d) dissolving in at least one antihyperthyroid drug;
(e) mixing in oleic acid and cooling.

It should be appreciated from the above description that there is provided a composition that includes an antihyperthyroid drug for use in treatment of hyperthyroidism in animals including cats.

The composition is particularly advantageous as it includes the antihyperthyroid drug in the form of a transdermal composition rather than as a tablet. As most cats and other animals are highly adverse to swallowing tablets, a transdermal formulation should significantly ease the difficulty in administering the antihyperthyroid drug.

A further advantage is that the composition of the present invention successfully delivers agent through the skin to the animal.

A yet further advantage is that the efficacy of the composition is comparable to existing tablet formulations or even provides superior results.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

The invention is now described further with reference to examples showing the efficacy of the formulation and showing variations in formulation that may be made within the scope of the present invention.

EXAMPLE 1

The purpose of this initial study was to determine whether antihyperthyroid drug (carbimazole) in two transdermal formulations could be absorbed in cats, and to compare the effects with the normal oral route of administration.

Materials and Methods

Four experimental cats were used, one of which turned out to have mild hyperthyroidism. They received standard oral carbimazole (Neomercazole, AFT Pharmaceuticals Ltd) tablets 5 mg administered twice daily for a week, followed by a test formulation of transdermal carbimazole (Test Formulation 1, Table 1, Example 2, below) 10 mg administered twice daily for a week, followed by Hoffman's (2002) transdermal formulation of carbimazole in poloxamer lecithin organogel (PLO), 10 mg administered twice daily for a week. At least a fortnight was allowed between treatments.

The cats had blood taken for total thyroxine (tT4) assays before and after each week's treatment, and for drug assays before and for 12 hours after the first treatment, and then at the end of the week's treatment. Blood was assayed for methimazole, as carbimazole is rapidly converted to methimazole once administered (Peterson and Aucoin, 1993).

Results

Figure 1:
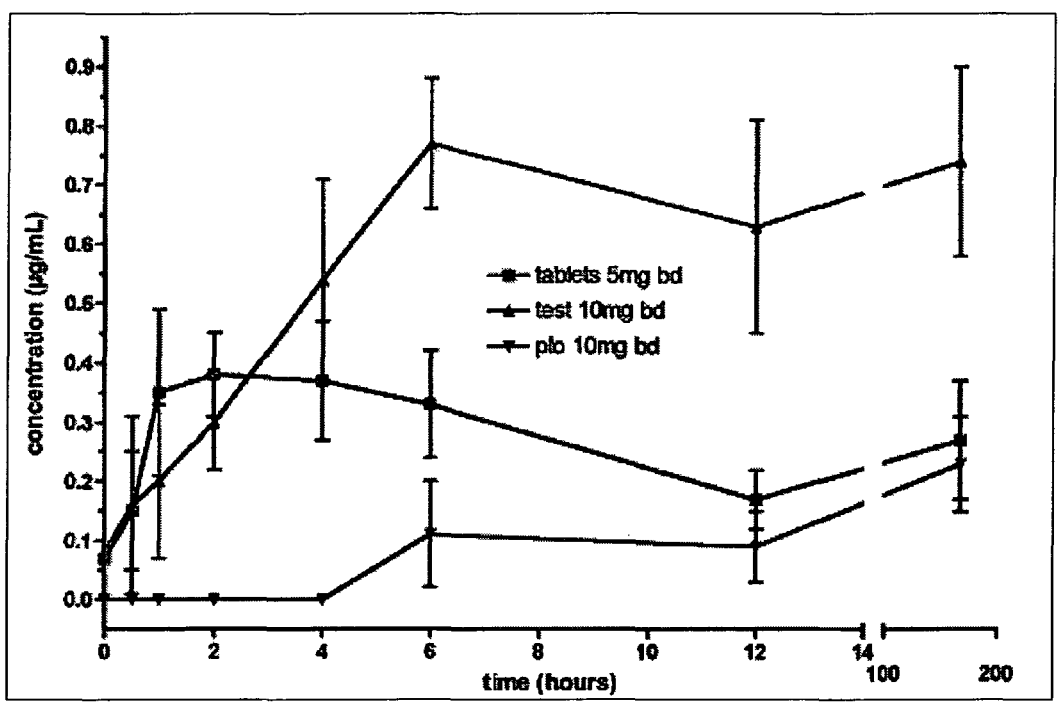
FIG. 1 shows a graph comparing carbimazole plasma levels over time in test animals used in Example 1; and, FIG. 2 shows a graph comparing thyroid enzyme levels over time in an experiment to test use of transdermal methimazole and carbimazole tablets.

The results are summarized in FIG. 1.

Oral administration of carbimazole produced slightly lower plasma levels (0.43±0.08 μg/mL) than published results with methimazole (0.51±0.15 μg/mL) (Hoffman et al, 2002), which decayed with a similar half life. tT4 concentrations were approximately halved over the seven days of the trial period.

The test transdermal formulation (Test Formulation 1, Table 1, Example 2, below), which was given at double the dose as poor absorption was expected, produced a $C_{max}$ 50% greater than the tablets, and an AUC almost double that seen for the orally administered tablets. The 7 day plasma level was also more than double that seen for the orally administered tablets. tT4 concentrations also halved over the seven days of the trial period.

The PLO formulation (also double the oral dose) produced barely detectable plasma concentrations over 12 hours, although the seven day plasma level was double the $C_{max}$ over the first 12 hours and similar to that produced by the tablets.

The test transdermal formulation gave comparable plasma levels as the tablets over the first two hours post administration and exceeded the plasma levels found for the tablets after four hours. This is in contrast to the PLO formulation which failed to show any plasma levels until six hours post administration, where they were still barely detectable. This result demonstrates a surprising speed of transdermal absorption in comparison to the PLO formulation.

None of the cats showed any adverse effects to any of the treatments, with the exception of slight reddening and scaling of the application site with both the transdermal preparations during one week.

Discussion

This study confirmed that oral carbimazole produces plasma methimazole levels in the published therapeutic range, and that carbimazole given transdermally in PLO does not provide therapeutic levels (in the short term at least). The formulation of the present invention provides plasma methimazole levels comparable to those after oral administration, and reduces tT4 by a similar amount.

EXAMPLE 2

Further formulations (Formulations 2 to 4) were produced using the same active agent (carbimazole).

In these formulations, carbimazole was used as the antihyperthyroid drug and transdermal agents were altered. D-limonene was substituted with either a pyrrolidone solvent (n-methyl-pyrrolidone, NMP), ethanol or triacetin.

More specifically, approximate formulations produced were as shown in Table 1 below.

TABLE 1

TEST FORMULATIONS 1 TO 4

| Ingredients | Formulation 1 % w/v | Formulation 2 % w/v | Formulation 3 % w/v | Formulation 4 % w/v |
|---|---|---|---|---|
| Carbimazole USP | 10.2 | 10.2 | 10.2 | 10.2 |
| PEG 4000 | 22 | 22 | 22 | 22 |
| Oleic acid | 9 | 9 | 9 | 9 |
| D-Limonene | 9 | 0 | 0 | 0 |
| Pharmasolve (NMP) | 0 | 9 | 0 | 0 |
| Ethanol | 0 | 0 | 9 | 0 |
| Triacetin | 0 | 0 | 0 | 9 |
| Propylene glycol | qs | qs | qs | qs |

The formulations were manufactured by the steps of:
1. Heating propylene glycol to approximately 50-60° C.;
2. Adding and dissolving. PEG 4000 while mixing (maintaining the temperature at approximately 50-55° C.);
3. Mixing in D-limonene, NMP, ethanol or triacetin depending on the formulation being prepared;
4. Adding and dissolving carbimazole while mixing;
5. Adding and mixing in oleic acid;
6. Allowing the mixture to cool to below 20° C. (overnight) to form a yellow coloured paste.

EXAMPLE 3

In a further example, Formulation 5 was produced including an alternative antihyperthyroid drug, methimazole. Methimazole is related to carbimazole, being a metabolite of carbimazole.

More specifically, Formulation 5 included ingredients as % w/v shown in Table 2 below.

TABLE 2

TEST FORMULATION 5

| Ingredients | % w/v |
|---|---|
| Methimazole USP** | 10.2 |
| PEG 4000 | 22 |
| oleic acid | 9 |
| Pharmasolve (NMP) | 9 |
| Ethanol | 0 |
| Triacetin | 0 |
| Propylene glycol | Qs |

EXAMPLE 4

In a further example, Formulation 6 was produced containing ingredients as %w/w as shown in Table 3 below.

TABLE 3

TEST FORMULATION 6

| Ingredients | % w/w |
|---|---|
| Methimazole USP** | 9.4 |
| PEG 4000 | 22 |

TABLE 3-continued

TEST FORMULATION 6

| Ingredients | % w/w |
| --- | --- |
| oleic acid | 9 |
| Pharmasolve (NMP) | 9 |
| Propylene glycol | 50.6 |

The formulation was manufactured by the steps of:
1. Heating propylene glycol to approximately 50-60° C.;
2. Adding and dissolving PEG 4000 while mixing (maintaining the temperature at approximately 50-55° C.);
3. Adding and mixing in Pharmasolve;
4. Adding and dissolving methimazole while mixing;
5. Adding and mixing in oleic acid;
6. Cooling the mixture to below 2-8° C.
7. Mixing at low speed for 1-2 hours maintaining the temperature below 15-20° C.

EXAMPLE 5

A further test formulation was produced utilizing butyl dioxitol (also known as Diethylene glycol monobutyl ether) as the penetration enhancer.

TABLE 4

TEST FORMULATION 7

| Ingredients | % w/v |
| --- | --- |
| Methimazole | 9.4 |
| PEG 4000 | 22 |
| Oleic acid | 9 |
| Butyl dioxitol | 9 |
| Propylene glycol | Qs |

The formulation was manufactured by the steps of:
1. Heating propylene glycol to 50-60° C.
2. Adding and dissolving PEG 4000 while mixing
3. Mixing in butyl dioxitol
4. Adding and dissolving methimazole while mixing
5. Adding and mixing in oleic acid
6. Cooling the mixture to 2-8° C. with mixing to form a pale yellow paste

EXAMPLE 6

A 1.8 kg pilot scale batch of the invention (Formulation 6) was prepared by the method of Example 4 and packaged into glass vials or High Density Polyethylene (HDPE) syringes. The packaged samples of the invention were stored under controlled conditions (25° C., 60% humidity) and tested for apparent density, syringibility and methimazole content at 3 month time intervals to asses the stability of the formulation.

The results of the measurements are summarized in Tables 5 and 6.

Measurements within the stated specifications were said to 'comply'.

TABLE 5

FORMULATION 6 STORED AT 25° C. AND 60% RH

| | Description | Apparent Density | Syringibility | Methimazole content |
| --- | --- | --- | --- | --- |
| Specification | A pale yellow smooth homogeneous paste | 1.050-1.125 @ 20° C. using a density bottle | Passes through 5 ml syringe | 9.0-11.0% w/v by HPLC |
| Initial | Complies | 1.081 | Complies | 10.3 |
| 3 months | Complies | 1.090 | Complies | 10.2 |
| 6 months | Complies | 1.083 | Complies | 10.0 |
| 9 months | Complies | 1.093 | Complies | 10.1 |

TABLE 6

FORMULATION 6 STORED AT 25° C. AND 60% RH

| | Description | Apparent Density | Syringibility | Methimazole content |
| --- | --- | --- | --- | --- |
| Specification | A pale yellow smooth homogeneous paste | 1.050-1.125 @ 20° C. using a density bottle | Passes through 5 ml syringe | 9.0-11.0% w/v by HPLC |
| Initial | Complies | 1.081 | Complies | 10.3 |
| 3 months | Complies | 1.090 | Complies | 9.9 |
| 6 months | Complies | 1.081 | Complies | 9.7 |
| 9 months | Complies | 1.090 | Complies | 9.8 |

EXAMPLE 7

A study was carried out to determine whether once daily administration of test Formulation 6 is safe and effective in treating naturally occurring cases of hyperthyroidism in cats.

Of 16 cats with newly diagnosed, naturally occurring hyperthyroidism which was judged suitable for medical treatment, 13 were treated with test formation 6 (10 mg dose once daily, applied to the inside of the pinna of the ear by the owner) and 3 were treated with oral tablets of carbimazole (Neomercazole, AFT Pharmaceuticals Ltd) (5 mg dose twice daily). The method of treatment was assigned randomly.

The cats in the study had no other significant diseases non-attributable to hyperthyroidism.

The cats were examined at 0,1,4,8 and 12 weeks for physical condition, body weight, haematology, serum biochemistry, urinalysis and tT4 concentrations. The efficacy of the treatments was assessed by clinical improvement and reduction in tT4 concentrations.

Figure 2:
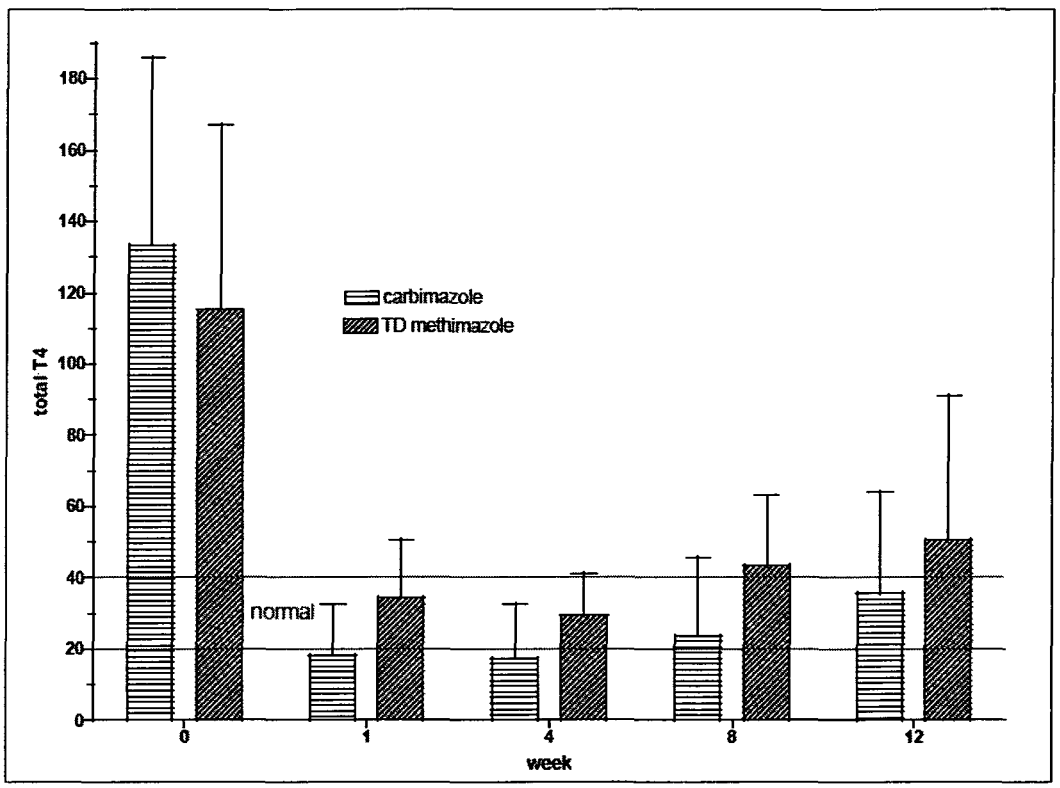

The results of the trial are summarized in FIG. 2

Discussion

The formulation of the present invention initially drops and then maintains tT4 levels at comparable rates and efficacy to oral carbimazole. The result is surprising since the treatment of the invention was only applied once daily whereas it is standard practice to give the oral carbimazole twice daily. This method gives considerable advantages for animal welfare given that the animal need not be administered a tablet twice daily which will often result in stress for the animal. Reducing the stress to the animal and owner as well as improving the convenience of the treatment will result in a more effective treatment method since the owner will be more likely to carry out and be consistent with the treatment plan.

In addition to the above efficacy and delivery advantages, Formulations 5 and 6 showed good stability when stored over time.

The above examples show that a variety of active agents and transdermal agents may be used whilst still producing a formulation with transdermal activity.

Aspects of the present invention have been described by way of example only and it should be appreciated that modifications and additions may be made thereto without departing from the scope thereof as defined in the appended claims.

REFERENCES

Buijtels J J. Kurvers I A. Galac S. Winter E A. Kooistra H S. Transdermal carbimazole for the treatment of feline hyperthyroidism. Tijdschrift voor Diergeneeskunde. 131(13):478-82, 2006

Feldman E C, Nelson R W Feline Hyperthyroidism. In: Canine and Feline Endocrinology and Reproduction (2nd ed). Philadelphia: W B Saunders, pp. 118-165, 1996

Hoffmann G, Marks S L, Taboada J, Hosgood G L, Wolfsheimer K J.: Transdermal methimazole treatment in cats with hyperthyroidism. J Feline Med Surg. 5(2): 77-82, 2003

Hoffman S B, Yoder A R, Trepanier L A. Bioavailability of transdermal methimazole in a pluronic lecithin organogel (PLO) in healthy cats. J Vet Pharmacol Ther. 25(3): 189-93, 2002

Lecuyer M. Prini S. Dunn M E. Doucet M Y. Clinical efficacy and safety of transdermal methimazole in the treatment of feline hyperthyroidism. Canadian Veterinary Journal. 47(2):131-5, 2006

Milner R J. Channell C D. Levy J K. Schaer M. Survival times for cats with hyperthyroidism treated with iodine 131, methimazole, or both: 167 cases (1996-2003). Journal of the American Veterinary Medical Association. 228(4):559-63, 2006

Murdan S. A review of Pluronic lecithin organogel as a topical and transdermal drug delivery system. Hospital Pharmacist. 12: 267-270, 2005

Naan E C. Kirpensteijn J. Kooistra H S. Peeters M E. Results of thyroidectomy in 101 cats with hyperthyroidism. Veterinary Surgery. 35(3):287-93, 2006

Peterson M E. Aucoin D P. Comparison of the disposition of carbimazole and methimazole in clinically normal cats. Research in Veterinary Science. 54(3): 351-5, 1993

Riviere J E, Papich M G. Potential and problems of developing transdermal patches for veterinary applications. Adv Drug Deliv Rev. 50(3): 175-203, 2001

Sartor L L, Trepanier L A, Kroll M M, Rodan I, Challoner L.: Efficacy and safety of transdermal methimazole in the treatment of cats with hyperthyroidism. J Vet Intern Med. 18(5): 651-5, 2004

Trepanier L A. Medical management of hyperthyroidism. Clinical Techniques in Small Animal Practice. 21(1): 22-28, 2006.

What we claim is:

1. A composition formulated for transdermal administration to a cat consisting of methimazole or a prodrug thereof as the active agent, and further comprising;
   22% w/w polyethylene glycol 4000;
   9% w/w oleic acid;
   9% w/w N-methyl-2-pyrrolidone or D-limonene; and
   propylene glycol as the non-active agents.

2. The composition as claimed in claim 1 wherein the composition contains approximately 5-10mg per dose of methimazole or a prodrug thereof.

3. The composition as claimed in claim 1 wherein the composition is formulated as a viscous gel or ointment.

4. A method of treatment of hyperthyroidism in a cat in need thereof comprising transdermal administration of the composition of claim 1.

5. A method for treating hyperthyroidism in an animal in need thereof comprising transdermally administering the composition of claim 1 formulated for transdermal administration.

6. A method of manufacturing the composition of claim 1 formulated for transdermal administration to a cat comprising the steps of:
   (a) heating propylene glycol to a temperature of 50-60° C.;
   (b) dissolving PEG 4000 into the propylene glycol;
   (c) mixing in at least one compound selected from the group consisting of d-limonene, and N-methyl-pyrrolidone;
   (d) dissolving in methimazole or a prodrug thereof; and
   (e) mixing in oleic acid and cooling.

7. The method as claimed in claim 4 wherein the dose of methimazole is 10 mg per day, administered once a day.

8. A composition formulated for transdermal administration to a cat consisting of
   9.4% w/w methimazole;
   22% w/w polyethylene glycol 4000;
   9% w/w oleic acid;
   9% w/w N-methyl-2-pyrrolidone;
   50.6% w/w propylene glycol.

* * * * *